United States Patent [19]

Metz

[11] Patent Number: 5,166,813
[45] Date of Patent: Nov. 24, 1992

[54] OPTICAL EVALUATION USING A HOLOGRAM BARRIER FILTER

[75] Inventor: Michael H. Metz, Yorktown Heights, N.Y.

[73] Assignee: Nygene Corporation, Yonkers, N.Y.

[21] Appl. No.: 551,634

[22] Filed: Jul. 11, 1990

Related U.S. Application Data

[63] Continuation of Ser. No. 489,876, Mar. 6, 1990, abandoned, which is a continuation of Ser. No. 200,137, May 31, 1988, abandoned.

[51] Int. Cl.⁵ .......................... G02B 5/32; G01J 1/58
[52] U.S. Cl. ........................................ 359/15; 359/1; 250/458.1; 250/459.1
[58] Field of Search ................... 350/3.7, 3.6; 250/458.1, 459.1; 359/1, 15, 3, 27

[56] References Cited

U.S. PATENT DOCUMENTS

| | | | |
|---|---|---|---|
| 4,560,233 | 12/1985 | Banbury | 350/3.7 |
| 4,671,603 | 6/1987 | McQuoid et al. | 350/3.7 |
| 4,786,125 | 11/1988 | Magarinos et al. | 350/3.7 X |

OTHER PUBLICATIONS

Kagelnik, H. "Coupled Wave Theory for Thick Hogogram Gratings" *The Bell System Technical Journal*, vol. 48, No. 9 Nov. 1969 pp. 2909-2947.

Masso, J. "Multilayer Thin Film Simulation of Volume Halograms" *SPIE-The International Society for Optical Engineering*, O-E Lase '88 Conference, Los Angeles Jan. 1988.

Courjon et al; "Noncoherent Microholography using a Holographic Optical Element as a Beamspliter"; *Optical Engineering* vol. 20, No. 2; Mar. 1981; pp. 233-236.

Courjon et al; "Enregistrement et Restitution Holographiques en Lumiére Blache Spatialement Incohérente"; *J. Optics*; vol. 9, No. 3, May 1978; pp. 157-162.

Potaturkin; "Incoherent diffration Correlator with a Holographic Filter"; *Applied Optics*, vol. 18, No. 24: Dec. 15, 1979; pp. 4203-4205.

Korbukov et al; "Two-Cascade Holographic Rejector Filter"; *Radiophysics & Quantum Electronics*, vol. 20 No. 5 Jan. 1978; pp. 481-486.

*Primary Examiner*—Bruce Y. Arnold
*Assistant Examiner*—David R. Parsons
*Attorney, Agent, or Firm*—Samuels, Gauthier & Stevens

[57] ABSTRACT

Optical detection apparatus and process which, in its optimum configuration, utilizes holographic optical elements both as a dichroic beamsplitter and as a selective notch-type barrier filter to enhance the amount of light to reach the detector while barring undesirable wavelengths from reaching the detector. The apparatus, when incorporated into a fluorescent-light detecting process, has the advantage of minimizing loss of light suffered because of a small Stokes shift, which shift occurs between the wavelength of the light transmitted to a sample target area and the increased wavelength of fluorescent light emitted from the sample for collection by a detection device. This advantage which is allowed by sharper cut-on of optical transmission properties relative to wavelength by a barrier filter (or filters) comprised of holographic optical element (or elements) provides an important increase in the fluorescence-collecting capacity of the apparatus and the sensitivity of detection processes carried out with the apparatus. Those optical detection systems which use a dichroic beamsplitter benefit by using a holographic optical element which can serve multiple purposes by acting as an exciter filter, selecting the wavelength band from the input light, as a highly efficient mirror to enhance the amount of light reaching the sample and, also, as a barrier filter as described above.

32 Claims, 7 Drawing Sheets

OPTICAL EVALUATION USING A HOLOGRAM BARRIER FILTER

This is a continuation of application Ser. No. 07/489,876, filed on Mar. 6, 1990, now abandoned, which is a continuation of application Ser. No. 07/200,137, filed on May 31, 1988, now abandoned.

BACKGROUND OF THE INVENTION

This invention relates to light-detecting apparatus, and processes, using high-efficiency volume reflection holographic elements for enhancing the sensitivity of wavelength selective optical-assaying processes such as assaying by fluorimetry. One advantage that can be achieved is increasing the amount of wavelength-shifted light that can be captured from a sample being optically-evaluated. This increase is achieved while the hologram efficiently acts as a barrier to undesirable wavelengths. In some configurations of the apparatus, a hologram increases the amount of light available to illuminate the sample.

A great deal of prior art has appeared in the two areas of art which are primarily utilized in the present invention —holographic optical elements (HOEs) and fluorescent detection technology. However, HOEs have been utilized only in some types of "beam-splitting" operations. See for example, U.S. Pat. No. 3,622,220 which describes a beamsplitter using a HOE. Other beamsplitting applications appear in U.K. Patent 2,021,803A and U.S. Pat. No. 3,767,310. All of these systems pertain to beamsplitting by transmissive diffraction and utilizing different orders of diffracted light as a plurality of beams. Such procedures are different from the splitting based on wavelength discrimination as will be described below.

Holographic barrier filters (wavelength selectors) are used in some form and are described in U.S. Pat. Nos. 4,601,533; 4,669,811; 4,655,540; and 4,582,389. One application of an HOE notch-type barrier filter is to provide eye protection to military personnel against laser beams.

An enormous amount of prior art on such materials is described in U.S. Patent Office Classification Class 350-3.7 but it is believed none of the art cited therein is more pertinent to the invention claimed herein—as that cited above. In the art cited, are a large number of publications on holograms, including such publications as that in Bell System Technical Journal of November 1969 "Coupled Wave Theory for Thick Hologram Gratings" by Herwig Kogelnik (Pages 2909-2947 and the thirty-eight references cited therein).

There is also some still unpublished material, which is not statutory prior art under U.S. law, e.g. a paper given by Jon D. Masso at the SPIE-The International Society for Optical Engineering, O-E Lase '88 Conference in Los Angeles (January 1988) and entitled "Multilayer Thin Film Simulation of Volume Holograms". The information therein is useful in indicating the problems encountered in providing "conventional", multilayer, barrier filters for narrowly selected frequencies. The number of deposited layers required for a notch-type barrier filter such as illustrated in the invention to be described below would be hundreds of, perhaps thousands of, barrier layers laminated in series to achieve the desired result.

In the prior art, instruments which examine a wavelength region different from those used to illuminate a sample, such as fluorometers, will incorporate several filters to tailor the input and output wavelength regions. An exciter filter is used to isolate a particular spectral region of the light source which is to illuminate a target sample. Such a filter is not required in a detection instrument which utilizes a a single line emission from a laser as the illumination source. A second filter, or barrier filter, is then used to isolate the wavelength region of interest emitted from the sample to pass to the detection system. The ideal barrier filter would cut off all of the exciting light and pass all of the sample emitted light in the wavelength region of interest. In addition, barrier filters are used to block other kinds of "noise" light such as Rayleigh, Tyndall and Raman scattering as well as other non-specific emissions from the sample, its container and the system optical elements. These filters are typically composed of colored or tinted glass or plastic with selective absorption characteristics; gelatin dyed with organic dyes, sometimes sandwiched between two pieces of glass; or interference filters made by serial deposition of metal or dielectric films onto a glass substrate. Often a glass cover plate is cemented over a deposited stack for protection. An exciter or barrier filter of the prior art may be comprised of several of the above mentioned filters each with a different wavelength selective characteristic stacked or cemented together to achieve the desired resultant selectivity.

Instruments, which examine sample characteristics at or near epi-reflection, such as fluorescence microscopes, require some overlap of input and output light paths. To accomplish this, dichroic beamsplitters are usually employed. These beamsplitters are typically long-pass filters, usually operating at 45 degrees to the incident light, and made by deposition of metal or dielectric films onto glass substrates. Common dichroic beamsplitter designs reflect wavelengths below a given center wavelength (illumination light) with an efficiency of typically around 90%, and transmit wavelengths above the center wavelength (sample fluorescence) with around 90% efficiency.

As an example, for their IMT-2 fluorescence microscope, the Olympus Corp. (Lake Success, N.Y.) recommends a dichroic beamsplitter (sold under their trade designation DM 500) with a barrier filter (sold under Olympus designation 0 515) for use with fluorescein isothiocyanate (FITC), a well known fluorescent labelling material. In many situations, (e.g. when using an Argon-Ion laser emitting at 488 nm as the illuminating source) such a filter combination is not very efficient at capturing the emission of light from a sample to be assayed, e.g. an FITC-tagged analyte which has a peak emission around 518 nanometers.

A color filter such as the 0 515 has a relatively slow cut-on, reaching its 50% point at 515 nm and not achieving near full transmission until around 550 nm. Thus much of the usable FITC emission is lost. Attempts to avoid the problems with such conventionally recommended filters have resulted in use of interference bandpass-type filters in some instruments. These are usually comprised of a number of metal or dielectric layers and spacers forming several Fabry-Perot interferometers, or filters, stacked together. Each filter of the stack is called a "cavity". Omega Optical, Inc. of Brattleboro, Vermont manufactures multiple cavity devices, known as their "discriminating filter" series, usually with 6 to 10 cavities for use with fluorescence instrumentation. Filters with Omega Optical's trade designations of 525DF35 and 540DF65 are recommended for use as barrier filters for FITC, where the first three numbers refer to the center wavelength and the last two to the bandpass of the filter. These filters exhibit a very steep cut-on with a fairly rectangular shape to the bandpass, and good blocking of excitation light (typically to optical densities of 4–6). Although the steeper cut-on of these filters allows proportionately more of the fluorescence to be collected near the emission peak, the limited passband prevents other regions of the emission spectrum to be collected, sometimes overcoming much of the advantage gained by the steep cut-on. In addition, use of such interference filters characteristically have the problem of incurring higher transmission losses, with transmissions typically averaging around 60% of the light incident on them, and considerably less when coupled with additional out of band blocking filters.

Clearly, there remains the desire for a relatively simple filter which allows capture of more emitted light and rejection of unwanted illumination light—usually an excess of illumination light of the source wavelength.

As indicated above, an important area of art related to one aspect of the present invention is fluorescent detection technology; e.g. immunoassays wherein some analyte to be detected is labelled either directly or indirectly by any of a variety of techniques with a fluorescent material which, when stimulated by an outside light source, emits a fluorescence which is detected as a measure of the fluorescent-tagged analyte to be assayed. There is a very large amount of prior art relating to detection of fluorescence. An area of particular interest to the inventor is assays wherein only a small amount of fluorescence need be detected or is available for detection. U.S. Pat. No. 4,537,861 to Elings and Nicoli contains a discussion of prior art relative to such art as immunochemical assay.

One prior homogeneous, e.g. in situ, technique suggested for measuring such fluorescence is the technique of determining a time-rate change in fluorescent signal. This technique is neither particularly convenient nor useful when the ratio of background to the binding fluorescence to be measured is not very low. Thus, U.S. Pat. No. 4,680,275 to Wagner et al discloses only a time-delay procedure for avoiding the presence of fluorescence background in a homogeneous test method and more selectively measuring the fluorescent light emitted from the sample area.

Another technique (e.g. the invention to which U.S. Pat. No. 4,537,861 to Elings and Nicoli relates) for a homogeneous non-isotopic immunoassay is the scanning of a spatial pattern which has been created by a plurality of spaced electrodes or magnets within (or adjacent to) the biochemical composition being assayed. The scanning is carried out in such a way that one can quickly distinguish between a substantially random background fluorescent output and a substantially non-random output associated with the labelled binding reaction which one wishes to detect.

Recently-issued U.S. Pat. No. 4,683,120 shows a centrifugally-assembled "patch" of material, the geometry of which is measured as a criterion of the nature of the composition from which it is assembled.

Also U.S. Pat. Nos. 4,731,337 and 4,115,535 to Luotola and Giaever respectively, each show various procedures for immunochemical assays.

The art of stimulating fluorescent light and processing it is well known in analytical chemistry. It is well described in U.S. Pat. No. 4,675,529 to Kushida, in the above-cited Wagner Patent and others of the references cited above.

Other art which may be related to some embodiment of the invention includes the use of fluorescently-tagged beads such as magnetic beads, glass beads, polymer beads, etc. By tagged beads is meant those that are directly tagged or those to which tagged materials attach. Among the vast amount of art relating to such materials are "New Immunolatex Spheres . . . " by Molday et al in J. Cell Biology, 64, 1985; "Application of Magnetic Microsphere . . . " by Molday et al, Nature Vol 268, 1977 and "Removal of Neuroblastoma Cells . . . " by Trellaven et al, Lancet; Jan. 14, 1984.

In any event, despite a great deal of work by earlier inventors with HOEs and fluorescent-detection technology, nobody conceived of wedding the two technologies together to achieve the highly sensitive assay process and detection equipment described below. Moreover, it is believed that nobody used the HOE technologies as disclosed below to enhance both the qualitative and quantitative optical detection of light from a sample.

Of course, the above discussion of the background invention is necessarily made with hindsight knowledge of the inventions disclosed for the first time herein. It is only with that knowledge that the diverse various references and articles of manufacture cited as background herein could have been assembled and discussed as "background" for the present invention.

SUMMARY OF THE INVENTION

It is an object of the invention to provide a highly sensitive optical detection process and apparatus for use in optical investigation of materials.

One object of the invention is to increase the portion of the excitation light reaching the material to be tested.

A particular object of the invention is to provide improved sensitivity when a portion of light leaving the sample must be removed before the remaining light is collected by the optical detecting apparatus.

Another object of the invention is to provide a highly sensitive optical detecting system which is particularly useful in fluorescence-stimulating optical detection procedures.

A further object of the invention is to provide a superior means for utilizing intense light sources such as lasers in optical evaluation processes.

A more particular object of the invention is to provide apparatus and processes which utilize the beneficial properties of volume reflection holograms as notch-type filters to achieve both a high transmittal of usefully-detected light emitted from a sample, especially a large portion of light that would—using conventional optical systems—normally be lost to a small Stokes shift between sample excitation, i.e. illumination light incident on the sample and light emitted from the sample.

Another object of the invention is to provide an improved means for utilizing epireflection of light from a target area.

An important object and process of the invention is to provide a particularly sensitive means for analyzing for very small quantities of biochemicals such as, e.g. ligands newly secreted by cells.

Other objects of the invention will be clear to those skilled in the art.

The above objects have been achieved by utilization of volume reflection holograms, as a barrier filter, a dichroic beamsplitter, and/or as an exciter filter, as components in optical detection processes and apparatus. In high efficiency volume reflection holograms the volume record of the holographic interference pattern (fringe pattern) usually takes the form of a spatial modulation of the index of refraction of the holographic medium, with little absorption. These high efficiencies are usually obtained using dichromated gelatin, as a material of construction, however other materials such as photopolymers have been used to make successful high efficiency volume reflection holograms. These holograms exhibit the property of strongly reflecting incoming light at or near the Bragg angle, while efficiently transmitting light not meeting the Bragg condition. Volume holograms and the Bragg condition are well described in the prior art. See Kogelnik, Bell System Technical Journal, Vol. 48, Page 2909 for a description thereof.

The properties of these holograms, such as reflection efficiency, and wavelength and angular bandwidths, are largely determined by controlling the thickness of the hologram, its index of refraction, the index of refraction modulation and the angle of the recording beams. Using typical values of thickness in the 10 to 30 micron range, index modulations up to 0.1 and an index of refraction of the medium in the 1.5 range, it can be shown using Kogelnik's coupled wave theory that transmissions as low as an optical density of 10 or more at the Bragg angle are theoretically possible. Holograms with optical densities in the 3 to 6 range and even as high as 9 have been shown to be practically and consistently achievable. In addition, such volume reflection holograms exhibit even steeper cut-on than the interference filters mentioned previously.

As barrier filters, high efficiency volume reflection holograms are of particular value in their ability to reject excitation light as well or better than standard optical components, while cutting on faster, and therefore passing more of the desired light to be detected, and having higher overall transmittance than conventional filters. These advantages are considerable when one has to measure small quantities of light for carrying out (or even making practical) many optical analyses. Conventional thin film interference filters could achieve passbands and wavelength/transmission cut-on slopes similar to holograms, but would require hundreds or even thousands of deposited layers to achieve the same result, and, as a consequence of such a construction be left with much higher out of band transmission losses.

A holographic dichroic mirror can serve as both beamsplitter and mirror. In detection processes, e.g. epifluorescence, wherein a beamsplitter is utilized, the beamsplitter, advantageously is formed of a volume reflection hologram, for the purpose of providing a highly-specific, wavelength-exclusion capability with exceptionally high efficiency of both the reflected and transmitted beams.

A particular advantage of the detection apparatus has been discovered for detecting light emitted by a sample being optically inspected which light has been wavelength-shifted (e.g., by a Stokes-shift) from the exciter light which is incident upon the area being evaluated.

In one embodiment of the invention, one involving epireflection or epifluorescence, two holograms are used in a light-detecting apparatus, one as a barrier filter and one as a dichroic beamsplitter. The resulting sensitivity is particularly important where it is desirable to measure small quantities of light emitted from the target area under analysis, for example in detecting fluorescence from very small quantities of fluorescently-labelled biochemicals.

In this embodiment, one hologram is used as a dichroic beamsplitter which is highly effective in selective reflection of the desired wavelength to be transmitted to the measurement area or target. Once the target has received the exciter light, it will be stimulated to emit a fluorescence—normally after a very short time elapses and normally at a different range of wavelengths than are contained in the exciter light. The emitted fluorescent light is transmitted through the dichroic beamsplitter and then through a second hologram, acting as a notch-type barrier filter. These two holograms reflect and dump undesired excitation light, (or target-illuminating light) reaching the holograms that have been reflected by the optics or the target area containing the analyte. The barrier filter characteristics are designed to allow a very substantial portion of the light emitted from the fluorescent sample to be transmitted to a photodetector, more light than typically can be collected when conventional optical detection filtering apparatus is used, particularly in processes using fluorophors which exhibit a small Stokes shift.

It will be understood from the foregoing that much of the advantage of the invention can be achieved also in non-fluorescing light-detection and analysis processes. Thus, for example, were one to wish to analyze a chemical composition such as a dye, a pesticide, or a herbicide, or the like, for the reflectivity at a certain wavelength (e.g. a wavelength that identifies the amount of an unstable chemical homolog in the dye or the amount of an excessively-toxic by-product in the herbicide or pesticide) that wavelength can be selectively detected with the highest precision by use of the presently-disclosed apparatus and process which not only achieves the highest incidence and selectivity of light being directed at the sample (by means of a high degree of reflectivity and selectivity of a dichroic beamsplitter) but also the highest selectivity and transmittance of reflected light emitted from that portion of the chemical composition which is being subjected to the detection process.

It is to be understood that the invention, when used for epifluorescence measurement and similar type optical systems, can be carried out using both a holographic dichroic beamsplitter and one or more barrier filters (which pass desired wavelengths and block undesirable wavelengths, e.g. the fluorescence excitation wavelengths, from reaching the detector. However it is also to be understood that great improvements in detection capability can be achieved with use of either one of a holographic dichroic beamsplitter or a holographic barrier filter. Indeed, use of both dichroic and barrier filters is only preferable in epifluorescent measurements when the dichroic does not block satisfactorily for the specific conditions. In some cases the barrier filters of different wavelength-rejecting characteristics can be used in series as barrier filters.

In an FITC epi-fluorescence measuring system, with the sample illuminated by Argon-Ion laser light at 488 nm, if one were to use a suitable holographic notch-type dichroic beamsplitter and barrier filter, each with an average transmittance between 500 and 700 nm of around 80%, for a given numerical aperture optical collection system, an improvement in fluorescence collection efficiency of around 36% would be realized over a similar system incorporating, say, an Olympus DM500 dichroic beamsplitter with an Olympus 0515 barrier filter. In addition, the gain in rejection of the illumination wavelength of the holographic system over the conventional filter system can be several to many orders of magnitude. Indeed, if such deep rejection of the illumination light is not necessary, the holographic barrier filter could be eliminated, resulting in a relative collection improvement of more than 50% over the non-holographic system.

High efficiency volume reflection holograms are typically produced in materials such as dichromated gelatin or photopolymers coated on a hard transparent substrate such as glass or plastic. A cover plate, usually of the same material as the substrate is cemented over the hologram, and the edges are sealed to protect it from dust, humidity and other adverse environmental conditions.

A typical volume-reflective substrate-mounted hologram structure useful in the invention can be specified by giving information, such as in the following example, to a manufacturer of said holograms, e.g. Flight Dynamics Inc. of Portland Oreg.:

| | Total Filter Specifications: |
|---|---|
| Dimensions: | 40 mm × 40 mm ± 1 mm |
| Clear Aperture: | 35 mm × 35 mm ± 1 mm |
| Thickness: | 6 mm ± 0.5 mm |
| Parallelism, Outer Surfaces: | < = 0.5 degrees |
| Construction: | Laminated and sealed with moisture resistance epoxy |
| | Substrate and Cover Plate Specifications: |
| Material: | Fused Silica |
| Nominal Thickness: | 3 mm |
| Cosmetic Surface Quality: | 80-50 scratch and dig |
| Flatness: | 1.5 waves over clear aperture at 488 nm |
| Coating: | Outer surfaces, broadband multilayer antireflection coating for less than 0.5% reflection at normal incidence between 500–650 nm. Center coating so that minimum reflection occurs at 518 nm. Coating shall withstand repeated cleanings with methanol and acetone using standard optical methods. |
| | Hologram Specifications: |
| Fringe planes: | parallel to surface |
| Incidence angle: | normal ± 1 degree |
| Wavelength Characteristics: | (specified by user for specific Application, see "Transmission. . .") |
| Optical Density at 488 nm: | ≧4 |
| Transmission Between 500–650 nm: | ≧80% average Tune hologram so that notch is centered below 488 nm to achieve maximal transmission at 500 nm while still maintaining optical density specified at 488 nm. |

Other specific optical systems may require additional specifications to fit special needs of its use, e.g. such as operating temperature ranges, conformation to certain military specifications, etc. Specifications for parts such as a dichroic beamsplitter would be similar except incidence angles should be noted as, for example, 45 degrees. In addition, care must be taken to match the polarization of the incident light and the angle sensitivity required, with the design of the holograms. For most applications, compliance with the coupled wave theory presented by Kogelnik, as previously mentioned will be sufficient for hologram design. Other, more exact theories in many formats can be found in the general optical literature. In fact, most suppliers of high efficiency volume reflection holograms could adequately respond to a request for a holographic laser-rejection filter of a certain size optimized for use at a given angle, to reject a specific wavelength band.

The apparatus and process of the invention finds particular value in systems comprising relatively strong exciter light sources such as a laser. In such circumstances, the ability of the new system to utilize such sources and also to achieve a much improved sensitive measurement of sample-emitted light is made possible by the high reflectivity of the excitation light by a volume-reflection hologram. Without such reflection efficiency, the optical detector could, in very many applications, be overwhelmed by the collection of excitation light. This is especially true in measurement of epifluorescence and transmitted fluorescence.

From what has been written above, it should be clear to those skilled in the art that the present invention can be of great use in a number of other specific modes. For example, instead of using a single hologram as a barrier filter for a given emittance measurement, one or more other such filters, properly specified for specific frequency-rejection characteristics, can be mounted for quick-switching into position for the purpose of independently detecting a plurality of different fluorescent emissions, e.g. as might be emitted by different fluorescent-tag compounds attached to different ligands in a culture wherein it is desirable to measure more than one parameter. Indeed, it is within the skill of hologram manufacturers to manufacture a hologram which has notches at two or more specific wavelengths.

When a laser is used as the source of the exciting light, the hologram-type dichroic beamsplitter acts as a highly effective mirror and can also deflect a large portion of exciter light reflected from the sample area. However, when a mercury lamp, tungsten lamp or other such light source having a wide range of wavelengths is used, the holographic dichroic beamsplitter can serve the dual purpose of functioning as an exciter filter, reflecting toward the sample only that portion of the light which encompasses the wavelength band that is required to illuminate the sample being evaluated.

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for the purposes of illustration in order that others skilled in the art will more fully understand the invention and the principles thereof and will be able to modify it and embody it in a variety of forms, each as may be best suited to the condition of a particular case.

BRIEF DESCRIPTION OF THE DRAWINGS

FIGS. 6 through 11 disclose a fluorescence-detecting application for the invention wherein the amount of analyte being detected can be very low.

DESCRIPTION OF THE PREFERRED EMBODIMENT(S)

Figure 1:
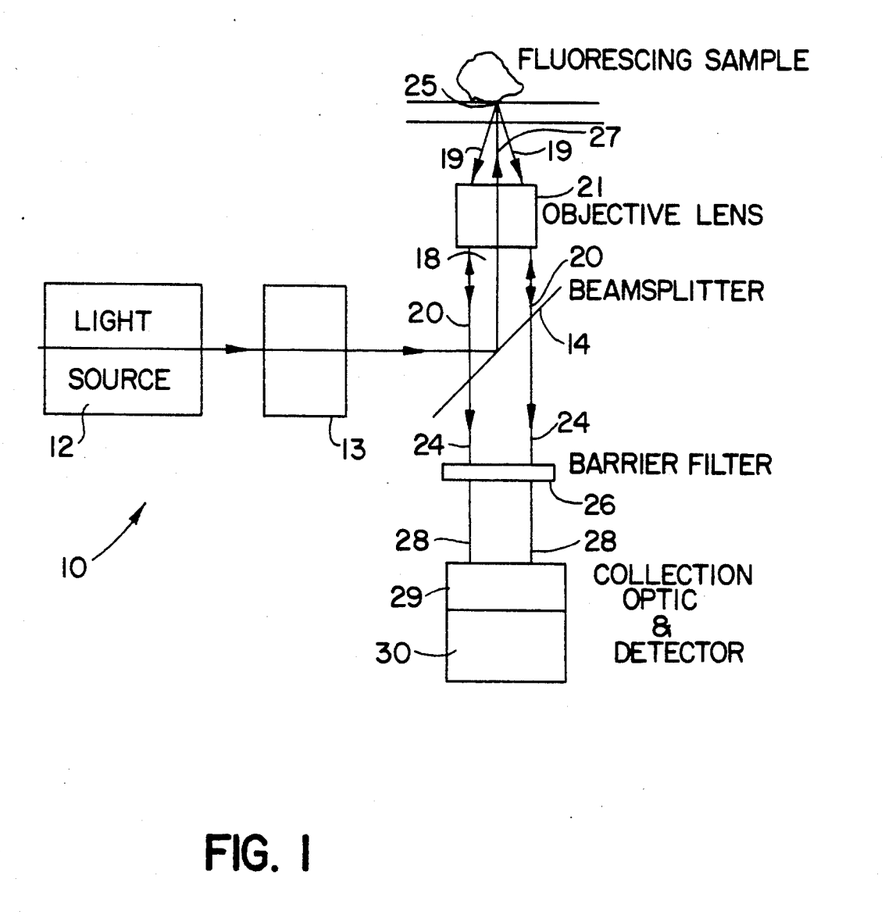
FIG. 1 is a schematic, optical diagram of an optical system of the invention.

FIG. 1 illustrates the general principle of the invention via the optical arrangement of apparatus 10. The light source illustrated, 12, is an Argon-Ion laser emitting at a wavelength of 488 nm being used as a fluorescence exciting light source. After passing through beam shaping optics and a narrow band laser line transmission filter at 13, the light falls on a HOE, a volume reflection hologram beamsplitter 14 (see FIG. 2) serving to reflect the 488 nm excitation light to illuminate the sample and allow passage of the emitted epi-fluorescence from the sample.

The 488 nm exciting light is reflected from the hologram along beam path 18 through an objective lens 21. The focused light beam 27 illuminates the target area 25 bearing a fluorescently-tagged analyte. In practice, this area can be a "spot" as small as about 0.1 millimeters in diameter or less. When measuring epifluorescence, a very substantial portion of the reflected light beam 27, along with light emitted from the target area (as a consequence of stimulation of fluorescence by the beam 19) returns along light paths 27 and is recollimated by objective 21 to produce beam 20 (which, although shown as two collimated rays is, in fact, transmitted along substantially the same path as beam 18). When this beam 20 hits the volume reflection holographic element forming dichroic beamsplitter 14, most of the reflected light of the laser's 488 nm wavelength is again reflected and dumped back toward the general direction of the laser light source, thereby substantially reducing the "noise" or extraneous (non-fluorescent) light that is transmitted through the hologram 14 as collimated beam 24. The beam 24 then passes through holographic barrier filter 26 for additional filtration of the excitation light and tailoring of the emitted fluorescent light 28 and is captured by a lens system 29 which focuses the light onto the detector 30.

Figure 3:
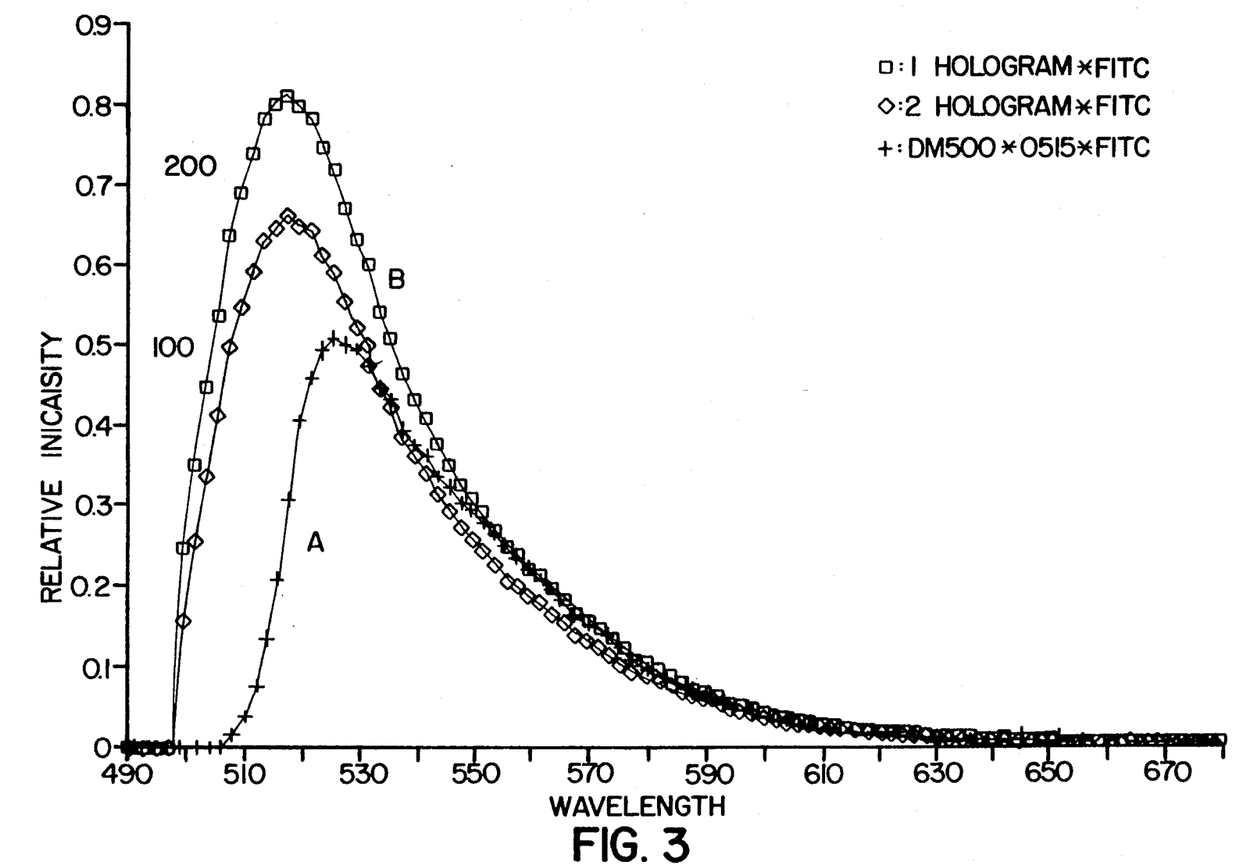
FIG. 3 is a graph indicating the improved optical-detection properties of a fluorescence-detecting procedure according to the invention compared to a typical prior art procedure.
Figure 4:
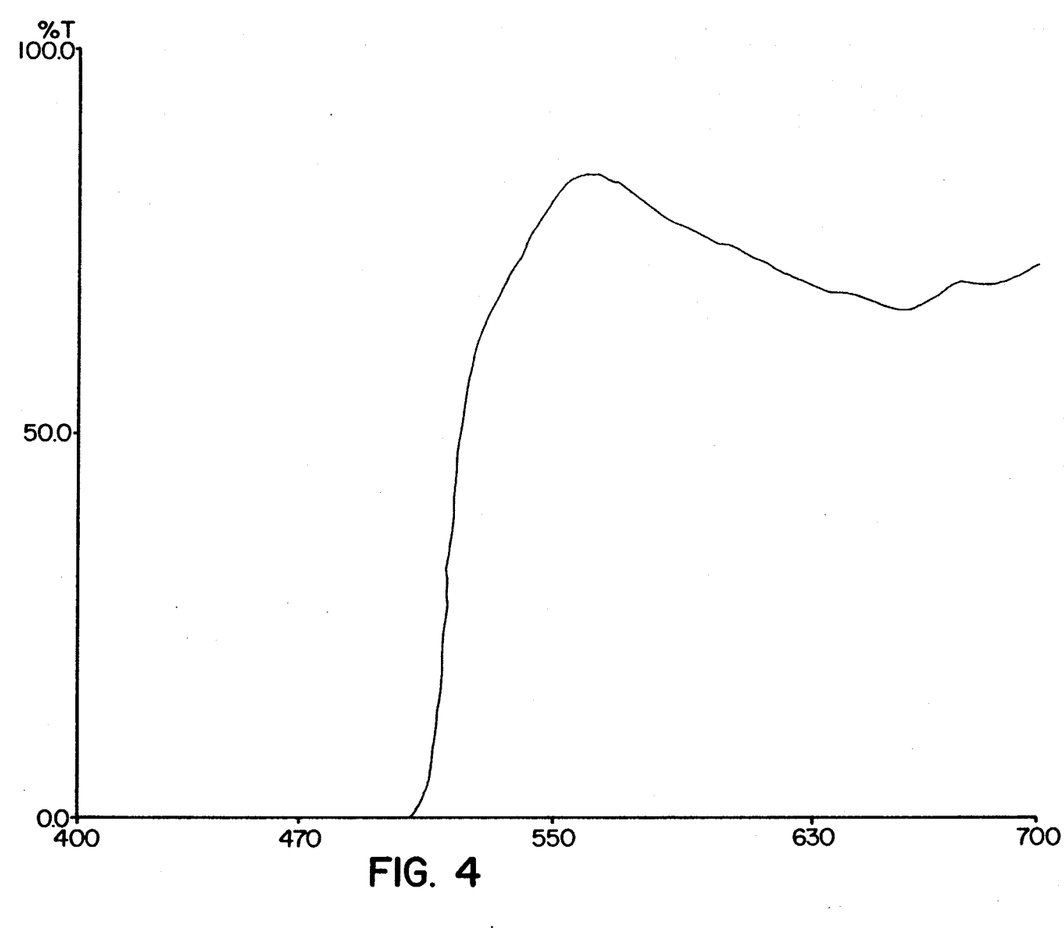
FIG. 4 indicates, at different wavelengths, how much light is transmitted through a typical prior art optical system using an Olympus DM 500 dichroic and an Olympus 0 515 barrier filter.
Figure 5:
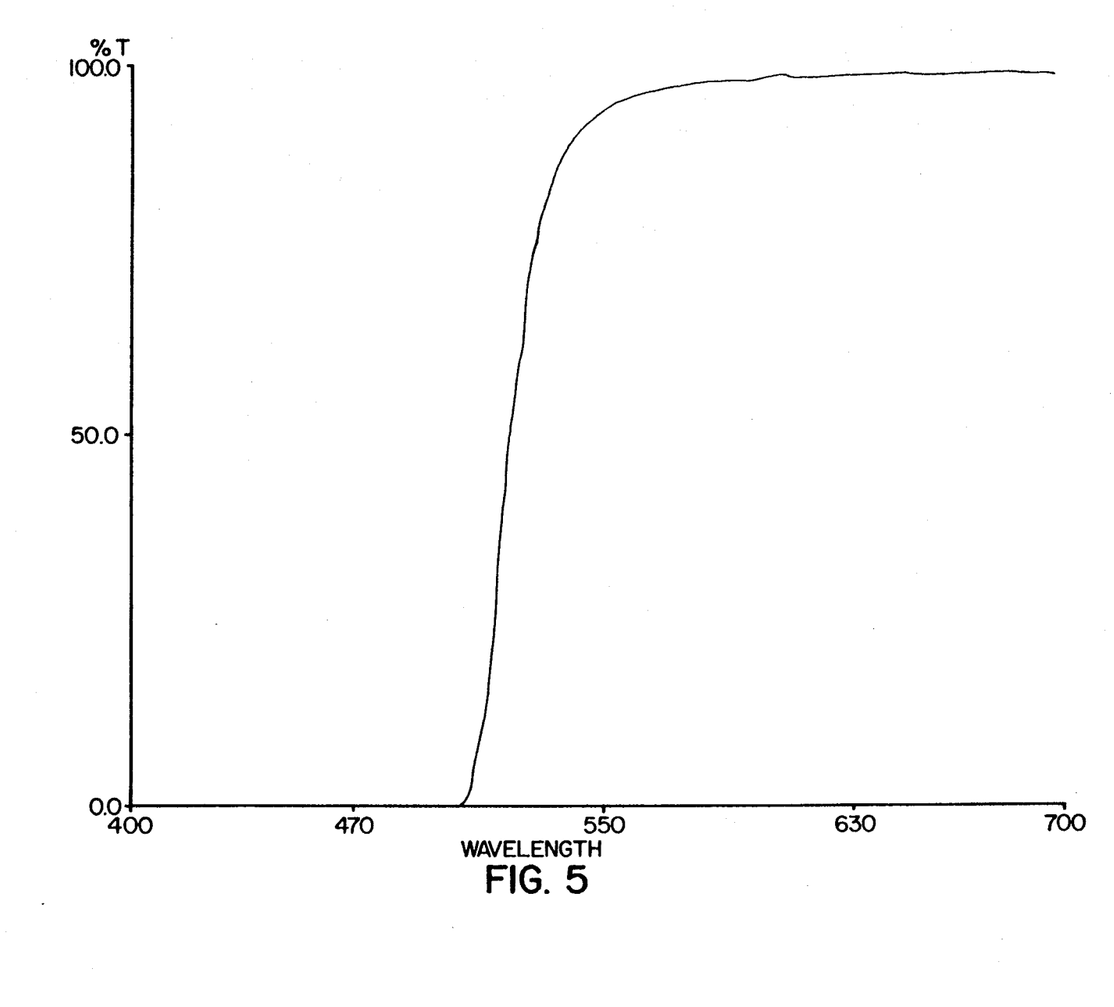
FIG. 5 indicates, at different wavelengths, how much light is transmitted through an Olympus O 515 barrier filter.

FIG. 3 is illustrative of the relative amount of fluorescent light transmitted from FITC to the photodetection system at various pertinent wavelengths through various prior art and novel light-processing systems. In reviewing these graphs it should be understood that:

A. is a curve defining light transmitted through an Olympus DM 500 dichroic filter, i.e. a conventional beamsplitter recommended for use in the particular fluorescence detection process, and an Olympus O 515 barrier filter;

B. is a system wherein two holograms are used, instead of using the Olympus beamsplitter and barrier filter described above.

Figure 2:
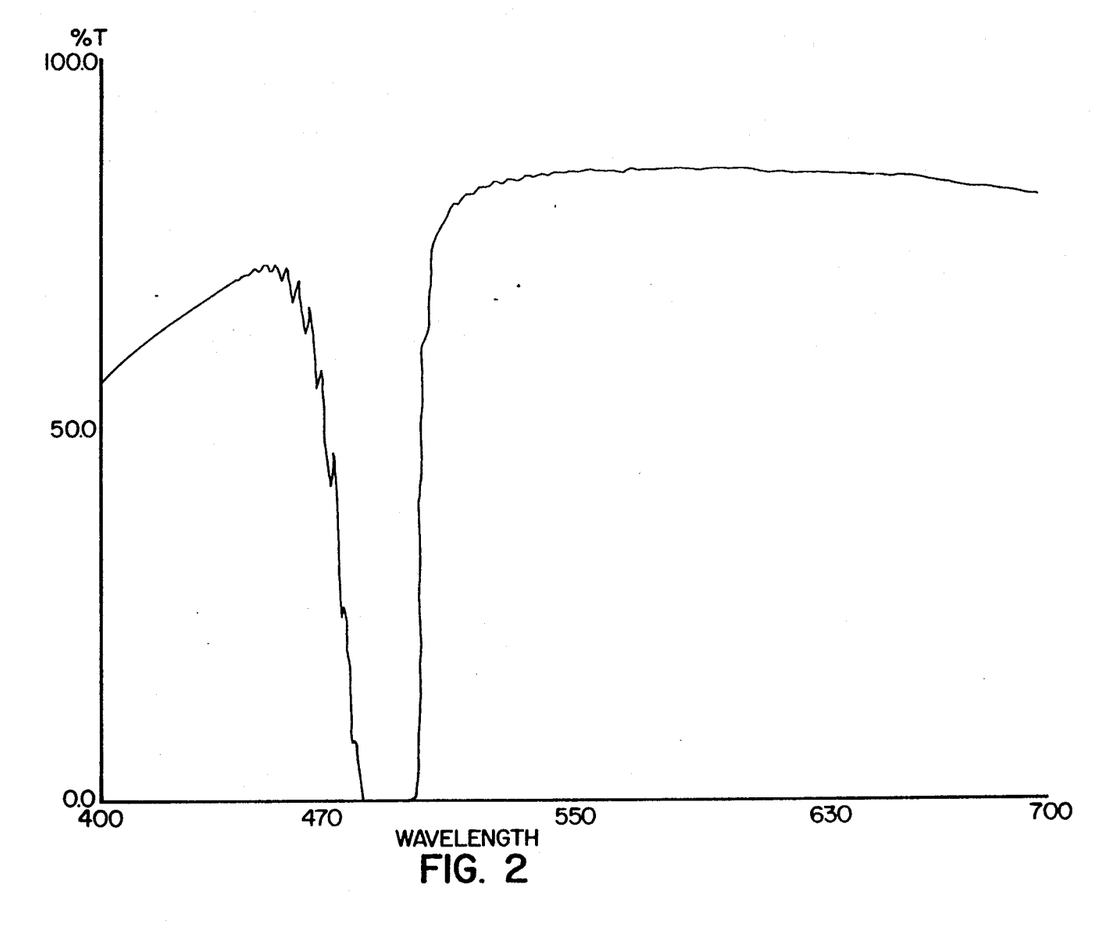
FIG. 2 is a graph indicating the transmittance of a typical hologram useful in practice of the invention.

C. is a curve defining light transmitted if one uses a hologram as defined in FIG. 2.

It is to be noted that the volume reflection holograms used in generating of FIG. 2 are not optimized, but merely the best available to the inventor at the time the data was generated. Indeed, the illustrated hologram is very good and well illustrates the invention. One object of a typical process is to reject as much exciting light, in this case the light of about 488 nanometers as is possible, but to transit as much emission light to the detector as is possible. In this case, the emission light to be optimized comes from an FITC probe (e.g. FITC conjugated to a protein) having an emission peak of about 518 nanometers in wavelength.

An examination of FIG. 3, e.g. the integral of the percentage of relative transmitted emission light over wavelengths between 500 and 550 nanometers shows that a great deal more of the FITC-emitted light is transmitted by the systems using hologram-type notch filters than by optical systems using only conventional barriers. This increase in the ability to select and detect emitted light from a sample area, becomes extremely important when one has very little emission light to detect. Even when the emitted light is larger in magnitude, the ability to detect more of it can be utilized to reduce the cost, size and complexity of the photo-collection and detection apparatus.

In the illustrative case, it is to be assumed that the analyte had been tagged with a fluorescing tag which emits fluorescent light with a peak wavelength of about 518 nanometers when stimulated by the exciting beam 27 which illuminates the target area. In such a situation, the volume-reflection holographic elements 14 and 26, acting as notch-type filters designed to reject the 488 nanometer wavelength selectively allow the emitted fluorescent wavelengths (500 to 600 nanometers) to pass therethrough along beam 28 and enter the detector 30 comprising collection optics and the photodetector. Many such devices are available to the prior art.

The practical effect of utilizing such holograms is very great. For example, the light reflected by beamsplitter 14 can be very nearly 100% of the 488 nanometer wavelength light entering it which one wishes to use to stimulate the fluorescence. Moreover, such conventional dichroic beamsplitters typically reflect only about 90% or so light. A similar result is achieved in dumping the reflected 488 nanometer light from the light beam 24 bearing the stimulated fluorescence from the target area containing the analyte. Thus, there is a marked decrease in unwanted noise and improved transmission of wavelengths above 488 nanometers to the detector.

However, as seen in FIG. 3, there is a substantial additional advantage to the invention, whenever there are small shifts in wavelength between emitted light and the exciting light. Such light falling within zones defined by areas 100 or areas 100 and 200 will be captured by the systems of the invention, but not by the prior art systems.

The following defines an Application for use of the invention which typifies the need to detect very small quantities of analyte, i.e. of fluorescence.

EXAMPLE 1

This assay demonstrates the detection of an antibody having a size in excess of 100,000 Daltons. However, it should be understood that far smaller ligands can be detected and that the detection method of the invention can recognize such analytes, properly conjugated to a probe, in extremely small numbers when appropriately targeted can identify even a single cell as a secreting cell very soon after the first secretion.

Figure 6:
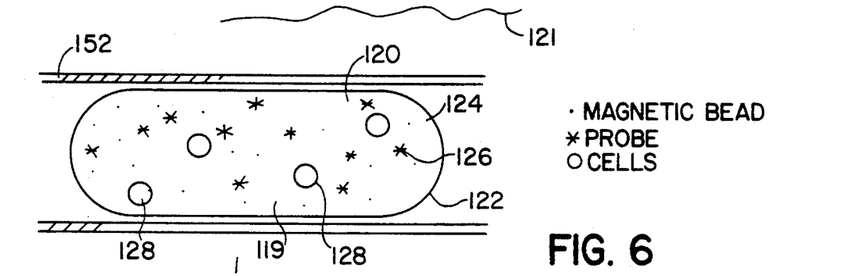
FIG. 6 is a schematic diagram showing a liquid biological culture containing hybridoma cells. The culture is isolated in a compartment within a plastic tubing, best seen in FIG. 9.

As seen in FIG. 6, polystyrene magnetic-beads 120, of nominal 1.75 micrometer diameter and supplied by the Seragen Company were coated by absorption with goat anti-mouse (GAM) IgG antibody (heavy and light chain type obtained from the Zymed Company). Bovine serum albumin (BSA) was used to block any further reactive sites on the magnetic-beads. Beads 120 will serve as a substrate for a probe which probe will be bound to the beads directly or indirectly and thereby made suitable for being pulled into an opaque patch. The beads were dispersed in a series of tubing-constrained reactor compartments such as 122, which contains a tissue culture medium 124. Also dispersed in compartment 122 is a so-called tag chemical, or probe, 126 which is an FITC-tagged goat anti-mouse polyclonal antibody, also obtained from Zymed, and some preselected hybridoma cells 128 (55.2 hybridoma cells producing $IgG_{2a}$). Before use, the cells are washed about four (4) times with Hanks balanced-salts solution to remove any free antibody. Other reactor compartments are prepared to contain either non-secreting 653 mouse myeloma cells as a negative control or $IgG_{2a}$ mouse myeloma protein (a product of ICN Corp.) which is used as a positive antibody control. Note the tubing 152 is held within an outer housing 121 which contains a gas atmosphere suitable for maintaining the desired atmosphere over the tube.

Figure 7:
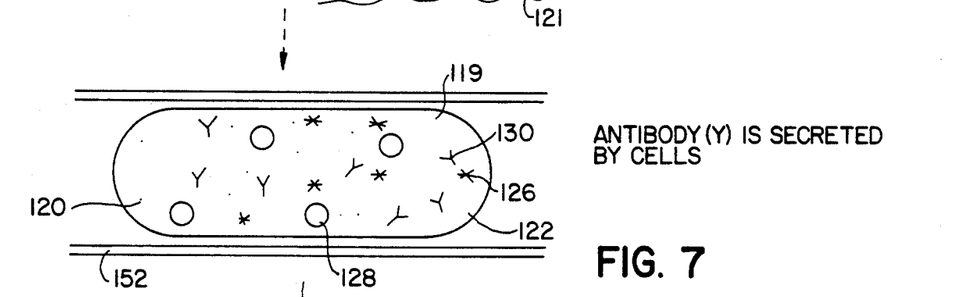
FIG. 7 illustrates the same culture as shown in FIG. 6 after antibodies are expressed by said cells.

FIG. 7 indicates a new situation wherein, after the passage of time, an antibody 130 is secreted from at least some of the cells 128, i.e. from a secretor cell.

Figure 8:
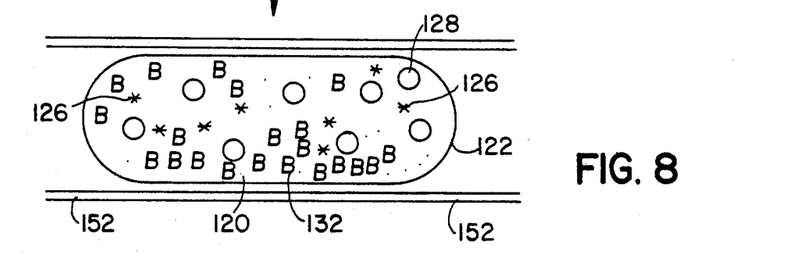
FIG. 8 is indicative of the same culture after there is substantial binding of both antibodies and a fluorescent probe to magnetic beads.

Magnetic-beads 120 through their coatings of goat anti-mouse antibody, which may be called MB/GAM, bind to the newly-secreted antibody 130 (which may be called Ab) as does the "probe" FITC-tagged goat antimouse polyclonal antibody 126 (which may be called GAM). The resulting complex is shown in FIG. 8 as a chemical composition 132 of the formula, using the terms set forth above:

MB/GAM - Ab - FITC/GAM

The probe-antibody 126 only associates with beads because of the mouse antibody thereon. In FIG. 8, "B" is the combined "composition" of magnetic bead, secreted antibody, and the probe.

Figure 9:
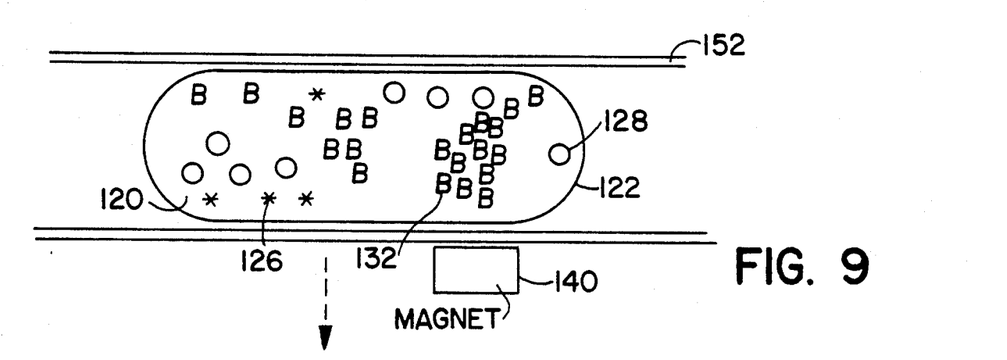
FIGS. 9, 10 and 11 show a magnetic material pulled into an opaque patch at the side of the compartment.
Figure 10:
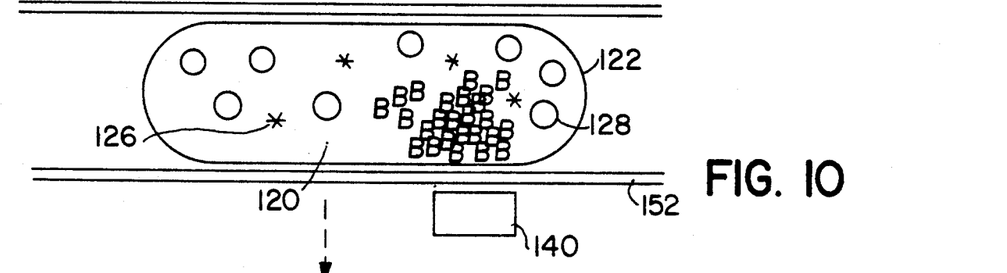
Figure 11:
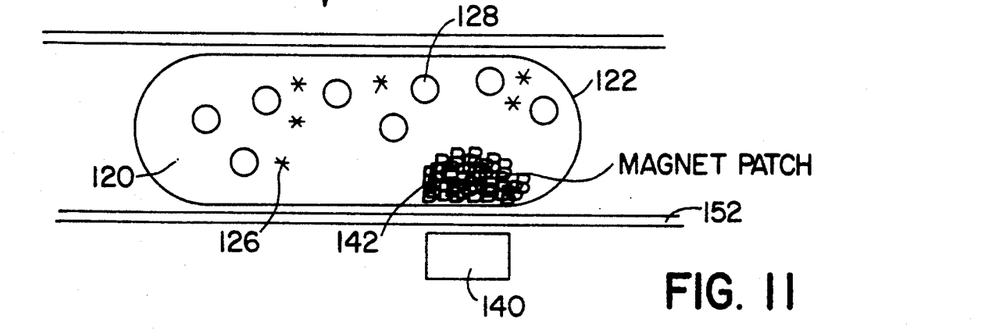

As seen in FIGS. 9 through 11, a magnet 140, a 7 kilogauss magnet which is about $1 \times 1.4 \times 7$ cm in size, is used to pull the magnetic particle bearing material over to a small area of the perimeter of compartment 122 and thereby to provide a substantially opaque population of such beads in a patch 142 as seen in FIG. 11.

The quantity of fluorescence emitted in response to a suitably-matched, stimulating light, as known in the art, will necessarily be directly related to the quantity of antibody secreted by cells 128 and which attach to both the MB/GAM and the FITC/GAM to form the MB/GAM - Ab - FITC/GAM material. Of course, if there is any magnetic material which has yet to attach to an antibody, it too will be contained in the magnetic patch 142, but it will not contribute to fluorescence.

All compartments contained treated magnetic-beads in a typical concentration of about $1.12 \times 10^8$ beads per milliliter. The concentration of beads can be much lower. The probe, is added to achieve a concentration of 375 nanograms of FITC/GAM per ml. From 4 to 250 hybridoma or non-secreting myeloma cells were initially placed in appropriate reaction compartments. The $IgG_{2a}$ mouse myeloma protein, supplied by ICN Corp., also combines with the magnetic-beads and fluorescent probe and is used as a positive control. It was placed in the other reactors at a concentration of 37.5 nanograms per ml.

Since the object of the above procedure is to identify the existence of secreting cells as soon as possible, and since the emitted fluorescence is specific for the existence of such secreted products, it is important that the smallest amount of the stimulated emission of fluorescence from the secreted products be measured so that an accelerated culturing and growth of the desired cell products can be started as soon as possible. The optical apparatus described herein is focused on the patch and the epifluorescence emitted from the sample is utilized as a measure of the analyte.

The magnetic beads serve as a good way to shield the target area surface being investigated from background fluorescence. The patch can also be used as an opaque shield against background with labelled beads such as glass by post-pulling the magnetic beads behind a patch of glass beads which has collected at the bottom of a compartment.

All of the following should be evident from FIG. 1:

A. If a relatively wide wavelength of exciter light is used, e.g. a tungsten lamp, then the dichroic will act as an exciter filter, reflecting only the wavelength segments for which it is designed. Of course, the exciter filter need not be a dichroic element, but a barrier filter designed to reject all but the desired excitation wavelengths.

B. It should also be realized that current holographic technology allows preparation of multi-notch-barrier, volume-reflection holograms. These can be used to allow the transmission of two or more separate wavelengths of light. This would be desirable, for example, when one wishes to obtain from the same culture, a measure of two different conjugated fluorescent probes, each emitting a different wavelength.

C. Although FIG. 1 refers to epireflection, the holograms can be efficiently used to block specific wavelengths—when the light is evaluated at an angle, e.g. 90 degrees, or when it is transmitted straight through a sample to a detector.

D. The target does not have to be held in a container. For example, it could be a geological mass such as a rock formation.

From the above discussion, it should be clear that high efficiency volume-reflection holograms can be used as barrier filters of the notch type, exciter filters, and dichroic beamsplitters. More particularly, depending upon the requirements of an optical system, it is to be realized that a single hologram can serve, among other combinations, as (a) an exciter filter and barrier filter;
(b) an exciter filter and a dichroic beamsplitter;
(c) a barrier filter and a dichroic beamsplitter; or
(d) an exciter filter, dichroic beamsplitter and a barrier filter.

On advantage of using high-efficiency volume reflection holograms is the ability, given a particular optical detection system of a green numerical aperture of being able to collect light more efficiently. Thus, at a given light-energy emission density, it will collect more light. This gives systems of the invention a greater ability to detect small quantities of light and to be useful with very small spot sizes. Thus, for example, illuminated areas subject to detection can be, if necessary, as small as a micron or smaller; indeed small enough to detect a very small number of, e.g., fluorescent probes as attached to ligands which one wishes to detect.

It is also to be understood that the following claims are intended to cover all of the generic and specific features of the invention herein described and all statements of the scope of the invention which might be said to fall therebetween.

What is claimed is:

1. An optical detection apparatus for use in measuring fluorescence emitted from a sample in a target area having a beamsplitter for directing light within a first wavelength or wavelength band from a light source to the target area to stimulate a sample, wherein the light emitted from the sample contains the first wavelength or wavelength band and a second wavelength or wavelength band characteristic of the sample; and a barrier filter for limiting the wavelengths of light to be returned from the target area or sample to a photodetector; the improvement wherein:
   a) said beamsplitter and said barrier filter comprise at least one volume reflection hologram which functions as a chromatic beamsplitter and which rejects all or a substantial portion of the first wavelength or wavelength band which is undesired to be passed to said photodetector, and passes all or a substantial part of the second wavelength or wavelength band or a third wavelength or wavelength band comprised of a portion of the second wavelength or wavelength band which is desired to be incident upon said photodetector.

2. An optical detection apparatus for use in measuring fluorescence emitted from a sample in a target area having a beamsplitter for directing light within a first wavelength or wavelength band from a light source to the target area to stimulate a sample, wherein light emitted from the target area or sample contains the first wavelength or wavelength band and a second wavelength or wavelength band characteristic of the sample; and for limiting the wavelengths of light to be returned from the target area or sample to a photodetector; the improvement wherein:
   a) said beamsplitter is a volume reflection hologram which functions as a chromatic beamsplitter which rejects all or a substantial portion of the first wavelength or wavelength band which is undesired to be passed to said photodetector, and passes all or a substantial part of the second wavelength or wavelength band which is desired to be incident upon said photodetector.

3. An optical detection apparatus for use in measuring fluorescence emitted from a sample in a target area having an exciter filter for limiting the wavelength or wavelength band emitted from a light source to a first wavelength or wavelength band to be incident upon a target area to stimulate a sample, a beamsplitter for directing light within said first wavelength or wavelength band from a light source to a target area to stimulate said sample, wherein light emitted from the sample contains all or part of the first wavelength or wavelength band and a second wavelength or wavelength band characteristic of the sample; and a barrier filter for limiting the wavelengths of light to be returned from the target area or sample to a photodetector; the improvement wherein:
   a) said exciter filter is a volume reflection hologram which functions as a chromatic beamsplitter; and
   b) said beamsplitter and said barrier filter comprise at least one volume reflection hologram which functions as a chromatic beamsplitter which rejects all or a substantial portion of the first wavelength or wavelength band which is undesired to be passed to said photodetector, and passes all or a substantial part of the second wavelength or wavelength band or a third wavelength or wavelength band comprised of a portion of the second wavelength or wavelength band which is desired to be incident upon said photodetector.

4. Apparatus as defined in claims 1, 2 or 3 wherein said light from said light source comprises light to stimulate the emission of fluorescence in an analyte within said target area and wherein said beamsplitter hologram selectively reflects said light to stimulate emission of fluorescence and selectively allows transmission of said emitted fluorescence from said target area to said photodetector.

5. An optical detection apparatus for use in measuring fluorescence emitted from a sample in a target area having a barrier filter for limiting the wavelengths of light returned from a sample to a photodetector, said sample which has been stimulated by light from a light source, said light within a first wavelength or wavelength band and light emitted from said sample contains said first wavelength or wavelength band and a second wavelength or wavelength band; the improvement wherein:
   a) said barrier filter is a volume reflection hologram which functions as a chromatic beamsplitter which rejects all or a substantial portion of the first wavelength or wavelength band which is undesired to be passed to said photodetector and passes all or a substantial portion of said second wavelength or wavelength band or a third wavelength or wavelength band comprised of a portion of the second wavelength or wavelength band which is desired to be incident upon said photodetector.

6. Apparatus as defined in claims 1, 3 or 5 wherein said light from said light source comprises light to stimulate the emission of fluorescence in the sample within said target area and wherein said barrier filter is a hologram which selectively reflects remaining undesired light which has reached said barrier filter and selectively allows transmission of desired light of said emitted fluorescence to said photodetector.

7. Apparatus as defined in claim 6 wherein said barrier filter hologram reflects two or more non-contiguous wavelengths or wavelength bands from said fluorescence to be detected by a photodetector or photodetectors.

8. Apparatus as defined in claim 6 wherein said barrier filter hologram transmits two or more non-contiguous wavelength or wavelength bands.

9. Apparatus as defined in claim 6 wherein two or more hologram barrier filters are cascaded to selectively allow two or more non-contiguous wavelengths or wavelength bands from said fluorescence to be detected by a photodetector or photodetectors.

10. Apparatus as defined in claim 6 wherein two or more of said hologram barrier filters are cascaded to selectively reflect two or more contiguous or overlapping wavelengths or wavelength bands to reduce the width of the wavelength band to be transmitted for detection by a photodetector or photodetectors, and thus allow a wider rejection wavelength bandwidth to be achieved than would ordinarily be practicable to be achieved from said volume reflection hologram.

11. Apparatus as defined in claim 6 wherein said barrier filter forms means to allow transmission of a substantial portion of light emitted from said target area, which emitted light has been subjected to a Stokes shift from a wavelength of light incident on said target area, to said photodetector.

12. Apparatus as defined in claims 1 or 2 wherein said beamsplitter hologram is of sufficient efficiency to function as both a beamsplitter and a barrier filter.

13. Apparatus as defined in claim 2 wherein said beamsplitter hologram functions as a beamsplitter, a barrier filter, and an exciter filter.

14. Apparatus as defined in claims 1, 2, 3 or 13 wherein said beamsplitter hologram reflects two or more non-contiguous wavelengths or wavelength bands to stimulate the emission of fluorescence from said sample with emission peaks at two or more wavelengths.

15. Apparatus as defined in claims 1, 2, 3 or 13 wherein said beamsplitter hologram transmits two or more non-contiguous wavelength or wavelength bands.

16. Apparatus as defined in claims 1, 2, 3 or 13 wherein two or more of said hologram beamsplitters are cascaded to selectively allow two or more non-contiguous wavelengths or wavelength bands to impinge upon said target area to stimulate said sample.

17. Apparatus as defined in claims 1, 2, 3 or 13 wherein two or more of said hologram beamsplitters are cascaded to selectively allow two or more contiguous or overlapping wavelengths or wavelength bands to impinge upon said target area to stimulate said sample, thus allowing a wider illuminating wavelength bandwidth to be achieved than would ordinarily be practicable to be achieved from said volume reflection hologram; or to selectively reject a wider wavelength bandwidth than would ordinarily be practicable to be achieved from said volume reflection hologram.

18. Apparatus as defined in claims 1, 2, 3 or 13 wherein two or more hologram beamsplitters are cascaded to selectively allow two or more non-contiguous wavelengths or wavelength bands to be transmitted for detection by one or more of said photodetectors.

19. Apparatus as defined in claims 1, 2, 3, and 13 wherein said beamsplitter forms means to allow transmission of a substantial portion of light emitted from said target area, which emitted light has been subjected to a Stokes shift from a wavelength or wavelength band of light incident on said target area, to said photodetector.

20. Apparatus as defined in claims 2 or 3 wherein said beamsplitter hologram functions as both a beamsplitter and an exciter filter.

21. Apparatus as defined in claims 2 or 3 wherein said volume reflection holograms are arranged to form an optical path between said target area and said detector to allow epireflection of a selected portion of light impinging on said sample in said target area and emitted from said sample or target area to be returned to said photodetector or photodetector.

22. An optical detection apparatus for use in measuring fluorescence emitted from a sample in a target area having an exciter filter for limiting the wavelength or wavelength band emitted from a light source to be incident upon a target area to stimulate a sample and a barrier filter for limiting the wavelengths of light to be returned from the target area or sample to a photodetector; the improvement wherein:
a) said exciter filter and said barrier filter comprise at least one volume reflection hologram which functions as a chromatic beamsplitter.

23. Apparatus as defined in claim 22 wherein said hologram functions as both an exciter filter and a barrier filter.

24. Apparatus as defined in claim 23 wherein said hologram reflects two or more non-contiguous wavelengths or wavelength bands to allow separated wavelengths or wavelength bands to illuminate said sample and/or allow separated wavelengths or wavelength bands from said fluorescence to be detected by a photodetector.

25. Apparatus as defined in claim 23 wherein said hologram transmits two or more non-contiguous wavelength or wavelength bands.

26. Apparatus as defined in claim 23 wherein two or more of said volume reflection holograms are cascaded to selectively allow two or more non-contiguous wavelengths or wavelength bands to illuminate said sample and/or allow two or more non-contiguous wavelengths or wavelength bands from said fluorescence to be detected by a photodetector or photodetectors.

27. Apparatus as defined in claim 23 wherein two or more of said holograms are cascaded to selectively reflect two or more contiguous or overlapping wavelengths or wavelength bands to increase the bandwidth of the light illuminating said sample, and/or to reduce the width of the wavelength band to be transmitted for detection by a photodetector or photodetectors, and thus allow a wider rejection wavelength bandwidth to be achieved than would ordinarily be practicable to be achieved from said volume reflection hologram.

28. A method for measuring fluorescence emitted from a sample in a target area which includes:
directing light from a volume reflection hologram which functions as a chromatic beamsplitter from a light source to a target area to stimulate a sample, said hologram, causing light in one or more contiguous or non-contiguous wavelengths or wavelength bands to stimulate said sample and emitting light from said target area or sample said light containing one or more wavelengths or wavelength bands and an additional contiguous or non-contiguous one or more wavelengths or wavelength bands, said additional wavelengths or wavelength bands being characteristic of the excited sample.

29. A method for measuring fluorescence emitted from a sample in a target area wherein the light returned from said target area is comprised of one or more contiguous or non-contiguous wavelengths or wavelength bands of those used to stimulate said sample and one or more contiguous or non-contiguous additional wavelengths or wavelength bands characteristic of the sample; which includes:
rejecting selectively the undesired light wavelengths or wavelength bands returned to said target area or sample with a volume reflection hologram which functions as a chromatic beamsplitter and passing selectively the desired light wavelengths or wavelength bands to be incident upon a photodetector or photodetectors.

30. A method as defined in claims 28 or 29 which further includes stimulating a sample within the target area; rejecting selectively undesired light returned from said target area wherein one or more of said volume reflection holograms which direct light to stimulate a sample in a target area, and one or more of said holograms which reject undesired light returned from said sample or target area are one and the same.

31. The method of claim 30 which further includes: rejecting selectively the undesired light wavelengths or wavelength bands returned from said target area or sample with a volume reflection hologram, the desired light wavelengths or wavelength bands to be incident upon a photodetector.

32. The method of claim 30 which further includes: effecting the directing of the light and the selective rejection of the undesired light with a single volume reflection hologram.

* * * * *